(12) United States Patent
Nishioka

(10) Patent No.: US 6,936,829 B2
(45) Date of Patent: Aug. 30, 2005

(54) IMAGE READ-OUT METHOD AND APPARATUS

(75) Inventor: Yukinori Nishioka, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 84 days.

(21) Appl. No.: 10/419,171

(22) Filed: Apr. 21, 2003

(65) Prior Publication Data

US 2003/0198272 A1 Oct. 23, 2003

(30) Foreign Application Priority Data

Apr. 19, 2002 (JP) ........................ 2002-118065

(51) Int. Cl.⁷ ............................ H01S 3/08; G01N 21/64
(52) U.S. Cl. ................................. 250/459.1; 372/101
(58) Field of Search ..................... 250/458.1, 484.4, 250/459.1, 327, 484.1; 372/101

(56) References Cited

U.S. PATENT DOCUMENTS

| | | | |
|---|---|---|---|
| 4,889,990 A | | 12/1989 | Hosoi et al. ............. 250/327 |
| 5,027,216 A | * | 6/1991 | Takanashi et al. ......... 347/129 |
| 5,028,793 A | * | 7/1991 | Lindmayer et al. ...... 250/484.4 |
| 5,434,882 A | * | 7/1995 | Chang .................... 372/92 |
| 5,767,887 A | * | 6/1998 | Warner et al. ............ 347/115 |
| 5,796,112 A | * | 8/1998 | Ichie .................... 250/458.1 |
| 6,277,533 B1 | * | 8/2001 | Wakamoto et al. .......... 430/30 |
| 6,617,590 B2 | * | 9/2003 | Nishioka et al. ......... 250/459.1 |
| 6,633,419 B2 | * | 10/2003 | Hosono et al. ............. 359/35 |
| 6,654,112 B2 | * | 11/2003 | Noguchi et al. ......... 356/237.3 |

FOREIGN PATENT DOCUMENTS

| | | |
|---|---|---|
| GB | 2246197 A | 1/1992 |
| JP | 59-15843 | 1/1984 |
| JP | 61-93538 | 5/1986 |
| JP | 1-60782 | 12/1989 |
| JP | 1-60784 | 12/1989 |
| JP | 4-3952 | 1/1992 |

* cited by examiner

*Primary Examiner*—Don Wong
*Assistant Examiner*—Hung Tran Vy
(74) *Attorney, Agent, or Firm*—Sughrue Mion, PLLC

(57) ABSTRACT

With an optical head, a stimulating ray beam produced by a stimulating ray source is irradiated onto an image carrier supported on a stage, and light emitted by the image carrier is collected and guided toward a photodetector. At least either one of the optical head and the stage is moved with respect to the other and in two-dimensional directions along a plane parallel with the other. The optical head comprises a concave mirror for reflecting the stimulating ray beam, which travels in parallel with the stage, toward the image carrier, and a lens for converging the stimulating ray beam, which has been reflected from the concave mirror, onto the image carrier. The lens and the concave mirror also guide the light, which is emitted by the image carrier, toward the photodetector.

15 Claims, 4 Drawing Sheets

IMAGE READ-OUT METHOD AND APPARATUS

BACKGROUND OF THE INVENTION

1. Field of the Invention

This invention relates to an image read-out method and apparatus, which are capable of being utilized commonly in an autoradiography image detecting system, a chemiluminescence image detecting system, an electron microscope image detecting system, a radiation diffraction image detecting system, and a fluorescence image detecting system.

2. Description of the Related Art

It has been proposed to use stimulable phosphors as radiation detecting materials in radiation image diagnosing systems. Specifically, energy from radiation carrying image information of an object is stored and recorded on a stimulable phosphor, which is contained in a stimulable phosphor layer of a stimulable phosphor sheet. The stimulable phosphor layer of the stimulable phosphor sheet, on which the radiation image information has been stored, is then exposed to an electromagnetic wave acting as stimulating rays, which cause the stimulable phosphor to emit light in proportion to the amount of energy stored on the stimulable phosphor during its exposure to the radiation. The light emitted by the stimulable phosphor, upon stimulation thereof, is photoelectrically detected and converted into a digital image signal. The digital image signal is then processed and used for the reproduction of the radiation image information of the object as a visible image on a recording material.

Also, it has been proposed to use stimulable phosphors as radiation detecting materials in autoradiography image detecting systems. Specifically, a substance imparted with a radioactive label is administered to an organism, and the organism or part of a tissue of the organism is taken as a sample. The sample and a stimulable phosphor sheet provided with a stimulable phosphor layer are superposed one upon the other for a predetermined length of time, and energy from the radiation emitted by the radioactive label contained in the sample is thus stored on the stimulable phosphor contained in the stimulable phosphor layer of the stimulable phosphor sheet. The stimulable phosphor layer of the stimulable phosphor sheet, on which the radiation image information of the sample has been stored, is then exposed to an electromagnetic wave acting as stimulating rays, which cause the stimulable phosphor to emit light in proportion to the amount of energy stored on the stimulable phosphor during its exposure to the radiation. The light emitted by the stimulable phosphor, upon stimulation thereof, is photoelectrically detected and converted into a digital image signal. The digital image signal is then processed and used for the reproduction of the radiation image information of the sample as a visible image on a recording material. The autoradiography image detecting systems are disclosed in, for example, Japanese Patent Publication Nos. 1(1989)-60782, 1(1989)-60784, and 4(1992)-3952.

Further, it has been proposed to use stimulable phosphors as light detecting materials in chemiluminescence image detecting systems, the stimulable phosphors having the characteristics such that the stimulable phosphors absorb and store energy from light during exposure to the light and, when the stimulable phosphors are then stimulated by an electromagnetic wave having wavelengths falling within a specific wavelength range, the stimulable phosphors emit light in proportion to the amount of energy stored on the stimulable phosphors during the exposure of the stimulable phosphors to the light. Specifically, a biopolymer whose protein sequence, nucleic acid sequence, or the like, has been fixed is selectively labeled with a labeling substance capable of producing chemiluminescence when being brought into contact with a chemiluminescence substrate. The biopolymer having thus been selectively labeled with the labeling substance capable of producing the chemiluminescence is then brought into contact with the chemiluminescence substrate. Also, energy from the chemiluminescence having wavelengths falling within the visible light wavelength range, which chemiluminescence is produced by the labeling substance when the labeling substance is thus brought into contact with the chemiluminescence substrate, is stored on the stimulable phosphor contained in the stimulable phosphor layer of the stimulable phosphor sheet. Thereafter, the stimulable phosphor layer of the stimulable phosphor sheet, on which the chemiluminescence image information of the biopolymer has been stored, is then exposed to an electromagnetic wave acting as stimulating rays, which cause the stimulable phosphor to emit light in proportion to the amount of energy stored on the stimulable phosphor during its exposure to the chemiluminescence. The light emitted by the stimulable phosphor, upon stimulation thereof, is photoelectrically detected and converted into a digital image signal. The digital image signal is then processed and used for the reproduction of the chemiluminescence image information of the biopolymer as a visible image on a recording material. The chemiluminescence image detecting systems are disclosed in, for example, U.S. Pat. No. 5,028,793 and British Patent Publication GB No. 2,246,197A.

Furthermore, it has been proposed to use stimulable phosphors as electron beam detecting materials in electron microscope image detecting systems, the stimulable phosphors having the characteristics such that the stimulable phosphors absorb and store energy from an electron beam during exposure to the electron beam and, when the stimulable phosphors are then stimulated by an electromagnetic wave having wavelengths falling within a specific wavelength range, the stimulable phosphors emit light in proportion to the amount of energy stored on the stimulable phosphors during the exposure of the stimulable phosphors to the electron beam. Specifically, the electron beam is irradiated to a metal sample or a nonmetal sample, and an electron beam diffraction image or an electron beam transmission image of the sample is detected. The thus detected image is utilized for an element analysis, a sample composition analysis, a sample structure analysis, and the like. Alternatively, the electron beam is irradiated to an organism tissue, and an image of the organism tissue is detected.

Also, it has been proposed to use stimulable phosphors as radiation detecting materials in radiation diffraction image detecting systems, the stimulable phosphors having the characteristics such that the stimulable phosphors absorb and store energy from radiation during exposure to the radiation and, when the stimulable phosphors are then stimulated by an electromagnetic wave having wavelengths falling within a specific wavelength range, the stimulable phosphors emit light in proportion to the amount of energy stored on the stimulable phosphors during the exposure of the stimulable phosphors to the radiation. Specifically, with the radiation diffraction image detecting systems, the radiation is irradiated to a sample, and a radiation diffraction image of the sample is detected. The thus detected image is utilized for a sample structure analysis, and the like.

The electron microscope image detecting systems and the radiation diffraction image detecting systems described above are disclosed in, for example, Japanese Unexamined Patent Publication Nos. 59(1984)-15843 and 61(1986)-93538, and U.S. Pat. No. 4,889,990.

The aforesaid various systems utilizing the stimulable phosphor sheets as the image detecting materials have the advantages in that chemical processing, such as development processing, need not be performed as in cases where photographic film is used. Also, the aforesaid various systems utilizing the stimulable phosphor sheets as the image detecting materials have the advantages in that various kinds of image processing are capable of being performed on the obtained image signals, and desired visible images are capable of being reproduced from the processed image signals. Further, the aforesaid various systems utilizing the stimulable phosphor sheets as the image detecting materials have the advantages in that quantitative analyses are capable of being performed by use of computers.

Further, fluorescence image detecting systems utilizing fluorescent substances as labeling substances in lieu of radioactive labeling substances in the autoradiography image detecting systems have heretofore been known. With the fluorescence image detecting systems, analyses of gene sequences and gene expression levels, separation and identification of proteins, and evaluation of molecular weights and characteristics of proteins are capable of being performed in accordance with information obtained by reading out fluorescence images. Specifically, for example, after a fluoro chrome has been added to a liquid containing a plurality of DNA fragments to be subjected to electrophoresis, electrophoresis of the plurality of the DNA fragments may be performed on a gel support. Alternatively, electrophoresis of a plurality of DNA fragments may be performed on a gel support containing a fluoro chrome. As another alternative, after electrophoresis of a plurality of DNA fragments has been performed on a gel support, the DNA fragments having been subjected to the electrophores is maybe leveled with a fluoro chrome by, for example, a process for dipping the gel support in a liquid containing the fluoro chrome, the fluoro chrome may then be excited with excitation light to produce fluorescence, the thus produced fluorescence may be detected, and a fluorescence image may thereby be formed. In accordance with the thus formed fluorescence image, a DNA distribution on the gel support is capable of being detected.

As a further alternative, with the fluorescence image detecting systems, after electrophoresis of a plurality of DNA fragments has been performed on a gel support, the DNA fragments having been subjected to the electrophoresis may be denatured. Thereafter, at least part of the denatured DNA fragments may be transcribed to a transcription support, such as nitrocellulose, with a Southern blotting technique. The denatured DNA fragments and a probe having been prepared by labeling a DNA or an RNA, which is complementary to a target DNA, with a fluoro chrome, may then be subjected to hybridization. In this manner, only a DNA fragment, which is complementary to the probe DNA or the probe RNA, is selectively labeled with the fluoro chrome. Thereafter, the fluoro chrome, with which the DNA fragment described above has been labeled, may be excited with the excitation light to produce the fluorescence, the thus produced fluorescence may be detected, and a fluorescence image may thereby be formed. In accordance with the thus formed fluorescence image, a target DNA distribution on the transcription support is capable of being detected.

As a still further alternative, with the fluorescence image detecting systems, a DNA probe, which is complementary to a DNA containing a target gene and has been labeled with a labeling substance, may be prepared. The DNA probe and a DNA on a transcription support may then be subjected to hybridization. Also, an enzyme may be subjected to binding with the complementary DNA having been labeled with the labeling substance, and the thus bound enzyme may then be brought into contact with a fluorescence substrate in order to convert the fluorescence substrate into a fluorescent substance, which is capable of producing the fluorescence. Thereafter, the fluorescent substance may be excited with the excitation light to produce the fluorescence, the thus produced fluorescence may be detected, and a fluorescence image may thereby be formed. In accordance with the thus formed fluorescence image, a target DNA distribution on the transcription support is capable of being detected.

The fluorescence image detecting systems have the advantages in that a radioactive substance need not be used, and the gene sequences, and the like, are capable of being detected in a simple manner.

The autoradiography image detecting systems, the chemiluminescence image detecting systems, the electron microscope image detecting systems, the radiation diffraction image detecting systems, and the fluorescence image detecting systems described above are utilized for the same purposes of use. Therefore, there is a strong demand for an image read-out apparatus, which is capable of being utilized commonly for the autoradiography image detecting systems, the chemiluminescence image detecting systems, the electron microscope image detecting systems, the radiation diffraction image detecting systems, and the fluorescence image detecting systems described above.

Accordingly, there has been proposed an image read-out apparatus capable of being utilized commonly for the autoradiography image detecting systems, the chemiluminescence image detecting systems, the electron microscope image detecting systems, the radiation diffraction image detecting systems, and the fluorescence image detecting systems described above, in which the stimulable phosphor sheets are utilized.

The image read-out apparatus proposed for use in the systems described above comprises an optical head for irradiating the stimulating rays (or the excitation light) to the image carrier, such as the stimulable phosphor sheet provided with the stimulable phosphor layer, the transcription support containing the sample labeled with the fluorescent substance, or the gel support containing the sample labeled with the fluorescent substance, and collecting the light emitted by the image carrier, such as the light, which is emitted by the stimulable phosphor contained in the stimulable phosphor layer when the stimulable phosphor is stimulated by the stimulating rays, or the fluorescence, which is produced by the fluorescent substance for the labeling of the sample when the fluorescent substance is excited by the excitation light. In order to scan the image carrier, the optical head is capable of being moved in two dimensional directions along a plane parallel with the image carrier.

Both the stimulating rays for stimulating the stimulable phosphor and the excitation light for exciting the fluorescent substance will hereinbelow be referred to as the stimulating rays.

As the optical head described above, an optical head comprising a plane mirror and a convex lens has been proposed. With the proposed optical head, the stimulating rays are reflected by the plane mirror toward the image carrier, and the reflected stimulating rays are irradiated via the convex lens to the image carrier. Also, the light emitted by the image carrier is collected by the convex lens and is guided by the plane mirror toward a photodetector. Specifically, the convex lens plays both the role for converging the stimulating rays, which have been produced by a stimulating ray source and are irradiated to the image carrier, and the role for collecting the light emitted by the image carrier. The convex lens is located such that the position of a focal point of the convex lens coincides with the surface of the image carrier. The optical head is thus constituted such that the convex lens collimates the light emitted by the image carrier, and the collimated light impinges upon the plane mirror. Also, as the stimulating rays, ordinarily, a laser beam having a small beam diameter is utilized. The laser beam has good converging characteristics. However, in order for an image having a high sharpness to be obtained, it is desired that the position of a beam waist of the stimulating rays coincides with the position of the surface of the image carrier. However, the position of the beam waist of the stimulating rays does not necessarily coincide with the position of the focal point of the convex lens, and therefore it often occurs that the position of the beam waist of the stimulating rays is located on the side spaced away from the surface of the image carrier toward the convex lens. In such cases, if the position of the beam waist of the stimulating rays and the position of the surface of the image carrier are set to be close to each other, the position of the focal point of the convex lens will be shifted from the position of the surface of the image carrier to a position on the side opposite to the convex lens. In cases where the position of the focal point of the convex lens is thus shifted, the light emitted by the image carrier cannot be collimated by the convex lens, and therefore the light emitted by the image carrier impinges in a divergent state upon the plane mirror. In such cases, the light emitted by the image carrier cannot be sufficiently collected and guided to the photodetector, and therefore the sensitivity of the image read-out apparatus cannot be kept high.

SUMMARY OF THE INVENTION

The primary object of the present invention is to provide an image read-out method, which is capable of being utilized commonly in an autoradiography image detecting system, a chemiluminescence image detecting system, an electron microscope image detecting system, a radiation diffraction image detecting system, a fluorescence image detecting system, and the like, and which is capable of yielding an image signal representing an image having good image quality and with a high sensitivity.

Another object of the present invention is to provide an apparatus for carrying out the image read-out method.

The present invention provides an image read-out method, comprising the steps of:

i) supporting an image carrier, which carries an image thereon, on a stage, ii) producing a stimulating ray beam by at least one stimulating ray source, iii) irradiating the stimulating ray beam, which has been produced by the stimulating ray source, onto the image carrier, which has been supported on the stage, by use of an optical head, the stimulating ray beam causing the image carrier to emit light carrying information of the image carried on the image carrier, iv) collecting the light, which is emitted by the image carrier, and guiding the light toward photo detecting means, the light collection and the light guiding being performed by the optical head, v) photoelectrically detecting the light, which is emitted by the image carrier, with the photo detecting means, and vi) moving at least either one of the optical head and the stage with respect to the other and in two-dimensional directions along a plane parallel with the other, wherein the optical head comprises:

a) a concave mirror for reflecting the stimulating ray beam, which has been produced by the stimulating ray source and travels in parallel with the stage, toward the image carrier, and b) a lens for converging the stimulating ray beam, which has been reflected from the concave mirror, and causing the converged stimulating ray beam to impinge upon the image carrier, and the lens and the concave mirror of the optical head guide the light, which is emitted by the image carrier, toward the photo detecting means.

The present invention also provides an image read-out apparatus, comprising:

i) at least one stimulating ray source for producing a stimulating ray beam, ii) a stage for supporting an image carrier, which carries an image thereon, iii) photo detecting means for photoelectrically detecting light, which is emitted by the image carrier, and iv) an optical head for:

irradiating the stimulating ray beam, which has been produced by the stimulating ray source, onto the image carrier, which has been supported on the stage, the stimulating ray beam causing the image carrier to emit light carrying information of the image carried on the image carrier, and collecting the light, which is emitted by the image carrier, and guiding the light toward the photo detecting means, and v) means for moving at least either one of the optical head and the stage with respect to the other and in two-dimensional directions along a plane parallel with the other, wherein the optical head comprises:

a) a concave mirror for reflecting the stimulating ray beam, which has been produced by the stimulating ray source and travels in parallel with the stage, toward the image carrier, and b) a lens for converging the stimulating ray beam, which has been reflected from the concave mirror, and causing the converged stimulating ray beam to impinge upon the image carrier, and the lens and the concave mirror of the optical head guide the light, which is emitted by the image carrier, toward the photo detecting means.

In the image read-out method and apparatus in accordance with the present invention, at least either one of the optical head and the stage is moved with respect to the other and in two-dimensional directions along the plane parallel with the other. Specifically, for example, the stage may be kept stationary, and the optical head may be moved with respect to the stage. Alternatively, the optical head may be kept stationary, and the stage may be moved with respect to the optical head. As another alternative, both the optical head and the stage may be moved with respect to each other.

Also, in the image read-out method and apparatus in accordance with the present invention, the image carrier maybe a support, on which an image of a fluorescent substance formed with a fluorescence image detecting system is carried. Alternatively, the image carrier may be a stimulable phosphor sheet, on which an autoradiography image is carried. As another alternative, the image carrier may be a stimulable phosphor sheet, on which an electron microscope image is carried. As a further alternative, the image carrier may be a stimulable phosphor sheet, on which a radiation diffraction image is carried. As a still further alternative, the image carrier may be a stimulable phosphor sheet, on which a chemiluminescence image is carried.

In the image read-out method and apparatus in accordance with the present invention, in cases where the autoradiography image, the electron microscope image, or the radiation diffraction image is to be carried on the stimulable phosphor sheet, the stimulable phosphor contained in the stimulable phosphor layer of the stimulable phosphor sheet may be selected from a wide variety of stimulable phosphors, which are capable of storing energy of the radiation or the electron beam and capable of being stimulated by an electromagnetic wave to emit light in proportion to the amount of energy stored thereon. However, the stimulable phosphor should preferably be selected from the stimulable phosphors, which are capable of being stimulated by light having wavelengths falling within the visible light wavelength range. Examples of the stimulable phosphors include the following:

an alkaline earth metal fluorohalide type of phosphor represented by the formula $(Ba_{1-x}, M^{2+}_x)FX:yA$ wherein $M^{2+}$ is at least one alkaline earth metal element selected from the group consisting of Mg, Ca, Sr, Zn, and Cd, X is at least one halogen selected from the group consisting of Cl, Br, and I, A is at least one trivalent metal element selected from the group consisting of Eu, Tb, Ce, Tm, Dy, Pr, Ho, Nd, Yb, and Er, x is a number satisfying $0 \leq x \leq 0.6$, and y is a number satisfying $0 \leq y \leq 0.2$, as disclosed in U.S. Pat. No. 4,239,968, an alkaline earth metal fluorohalide type of phosphor represented by the formula SrFX:Z wherein X is at least one halogen selected from the group consisting of Cl, Br, and I, and Z is Eu or Ce, as disclosed in Japanese Unexamined Patent Publication No. 2(1990)-276997, a europium activated composite halide type of phosphor represented by the formula $BaFX \cdot xNaX':aEu^{2+}$ wherein each of X and X' is at least one halogen selected from the group consisting of Cl, Br, and I, x is a number satisfying $0 < x \leq 2$, and a is a number satisfying $0 < a \leq 0.2$, as described in Japanese Unexamined Patent Publication No. 59(1984)-56479, a cerium activated trivalent metaloxy halide type of phosphor represented by the formula MOX:xCe wherein M is at least one trivalent metal selected from the group consisting of Pr, Nd, Pm, Sm, Eu, Tb, Dy, Ho, Er, Tm, Yb, and Bi, X is either one or both of Br and I, and x is a number satisfying $0 < x < 0.1$, as described in Japanese Unexamined Patent Publication No. 58(1983)-69281, a cerium activated rare earth element oxyhalide type of phosphor represented by the formula LnOX:xCe wherein Ln is at least one rare earth element selected from the group consisting of Y, La, Gd, and Lu, X is at least one halogen selected from the group consisting of Cl, Br, and I, x is a number satisfying $0 < x \leq 0.1$, as disclosed in U.S. Pat. No. 4,539,137, and a europium activated composite halide type of phosphor represented by the formula $M^{II}FX \cdot aM^{I}X' \cdot bM^{III}X''_2 \cdot cM^{III}X'''_3 \cdot xA:yEu^{2+}$ wherein $M^{II}$ is one alkaline earth metal element selected from the group consisting of Ba, Sr, and Ca, $M^{I}$ is at least one alkali metal element selected from the group consisting of Li, Na, K, Rb, and Cs, $M^{II}$ is at least one bivalent metal element selected from the group consisting of Be and Mg, $M^{III}$ is at least one trivalent metal element selected from the group consisting of Al, Ga, In, and Tl, A is at least one metal oxide, X is at least one halogen selected from the group consisting of Cl, Br, and I, each of X', X'', and X''' is at least one halogen selected from the group consisting of F, Cl, Br, and I, a is a number satisfying $0 \leq a \leq 0.2$, b is a number satisfying $0 \leq b \leq 10^{-2}$, c is a number satisfying $0 \leq c \leq 10^{-2}$, and $a+b+c \geq 10^{-2}$, x is a number satisfying $0 < x \leq 0.5$, and y is a number satisfying $0 < y \leq 0.2$, as described in U.S. Pat. No. 4,962,047.

Also, in cases where the chemiluminescence image is to be carried on the stimulable phosphor sheet, the stimulable phosphor contained in the stimulable phosphor layer of the stimulable phosphor sheet may be selected from a wide variety of stimulable phosphors, which are capable of storing energy of light having wavelengths falling within the visible light wavelength range and capable of being stimulated by an electromagnetic wave to emit light in proportion to the amount of energy stored thereon. Examples of the stimulable phosphors include a metal halophosphate type of phosphor, a rare earth element activated sulfide type of phosphor, an aluminate type of phosphor, a silicate type of phosphor, a fluoride type of phosphor, and a mixture of two or more of the above-enumerated phosphors. Among the above-enumerated phosphors, the rare earth element activated sulfide type of phosphor is preferable. In particular, a rare earth element activated alkaline earth metal sulfide type of phosphor disclosed in U.S. Pat. No. 5,029,253 or 4,983,834 is preferable.

With the image read-out method and apparatus in accordance with the present invention, wherein the optical head comprises the concave mirror and the lens, the advantages over the use of an optical head consisting of a plane mirror and a lens are capable of being obtained in that the position of the beam waist of the stimulating ray beam is capable of being set at a position close to the surface of the image carrier, and the sharpness of the obtained image is thus capable of being enhanced, and in that the light emitted by the image carrier is capable of being collected efficiently. With the optical head consisting of the plane mirror and the lens, the problems occur in that, in cases where the position of the image carrier and the position of the focal point of the lens are shifted from each other, the light emitted by the image carrier cannot be formed into a collimated light beam or a converged light beam only with the refracting power of the lens and impinges in the divergent state upon the plane mirror, and therefore the light having been reflected from the plane mirror travels in a more divergent state. However, with the image read-out method and apparatus in accordance with the present invention, wherein the optical head comprises the concave mirror and the lens, the emitted light incident in a divergent state is capable of being converged, and therefore the light emitted by the image carrier is capable of being guided efficiently toward the photo detecting means. Also, since the light collecting efficiency is thus capable of being enhanced, the image read-out operation is capable of being performed with a high sensitivity.

DESCRIPTION OF THE PREFERRED EMBODIMENTS

The present invention will hereinbelow be described in further detail with reference to the accompanying drawings.

Figure 1:
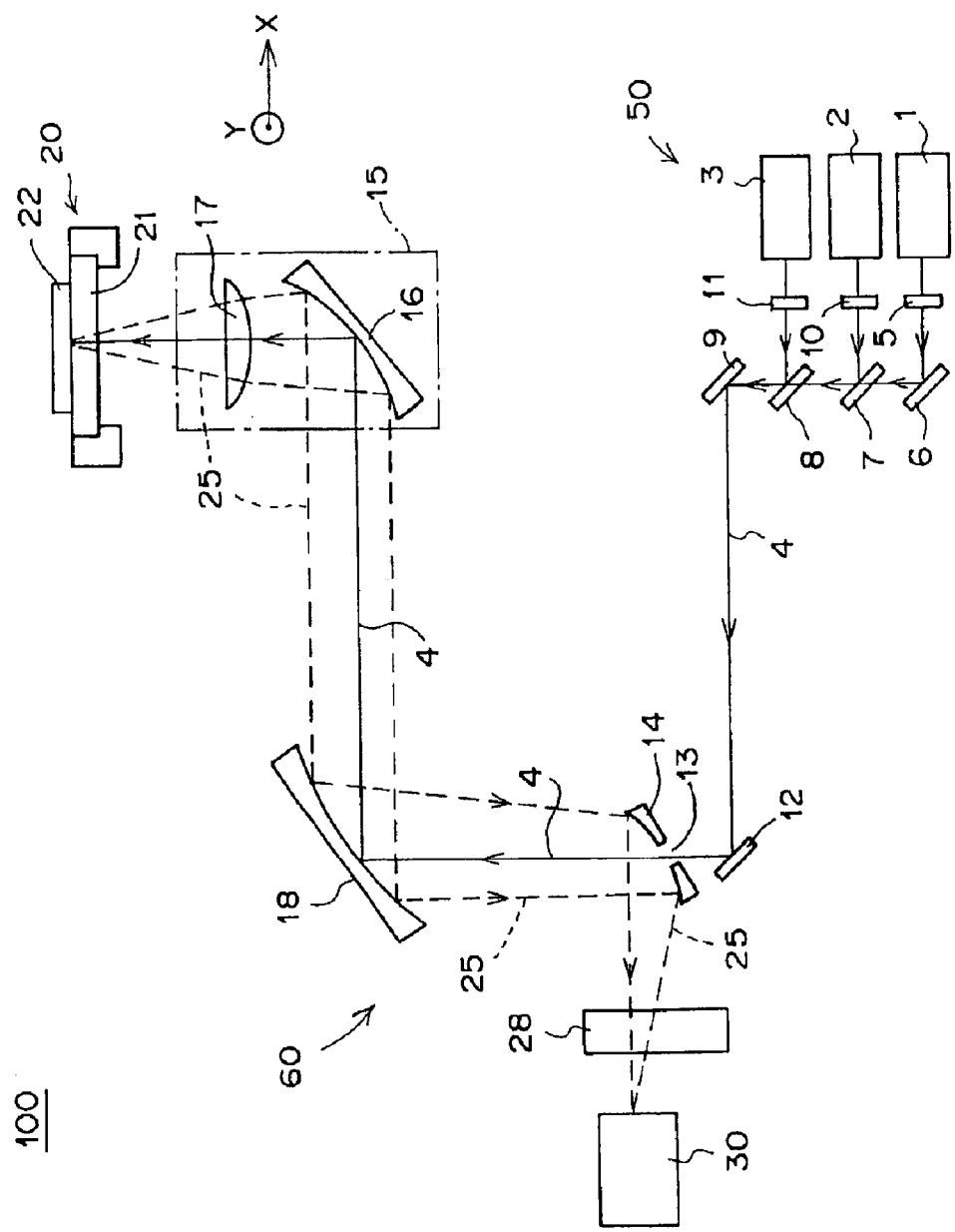
FIG. 1 is an explanatory view showing an embodiment of the image read-out apparatus in accordance with the present invention.
Figure 2:
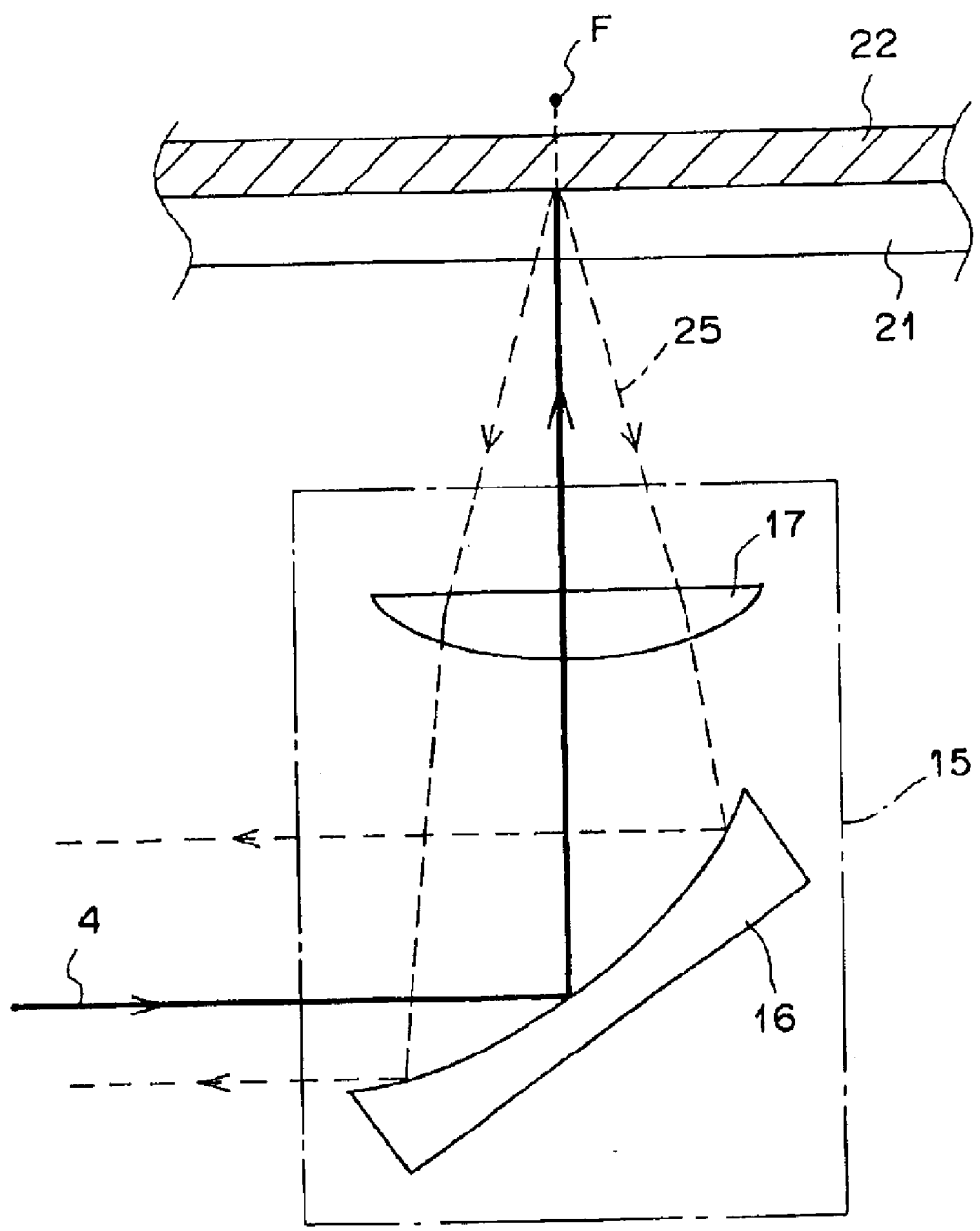
FIG. 2 is an enlarged side sectional view showing a constitution in the vicinity of an optical head in the embodiment of FIG. 1.
Figure 3:
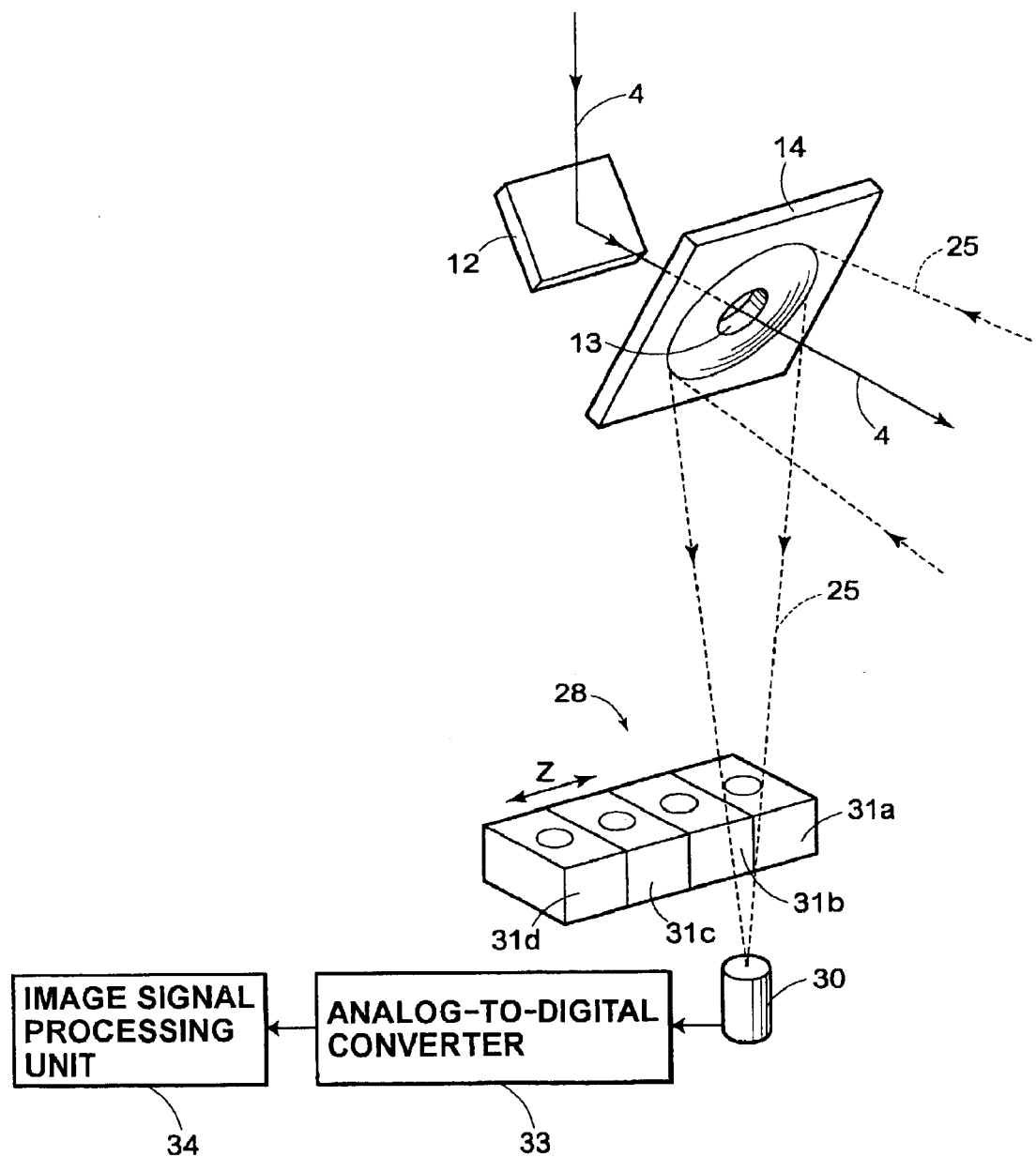
FIG. 3 is an enlarged schematic perspective view showing a constitution in the vicinity of a photomultiplier in the embodiment of FIG. 1.

FIG. 1 is an explanatory view showing an embodiment of the image read-out apparatus in accordance with the present invention. FIG. 2 is an enlarged side sectional view showing a constitution in the vicinity of an optical head in the embodiment of FIG. 1. FIG. 3 is an enlarged schematic perspective view showing a constitution in the vicinity of a photomultiplier in the embodiment of FIG. 1.

With reference to FIG. 1, an image read-out apparatus 100, which is an embodiment of the image read-out apparatus in accordance with the present invention, comprises a stage 20 provided with a glass base plate 21, on which an image carrier 22 carrying an image thereon is supported. The image read-out apparatus 100 also comprises an optical head 15 for irradiating a laser beam 4, which act as stimulating rays, onto the image carrier 22. The laser beam 4 acting as the stimulating rays causes the image carrier 22 to emit light 25 carrying information of the image carried on the image carrier. The optical head 15 also collects the light 25, which is emitted by the image carrier 22. The image read-out apparatus 100 further comprises a stimulating ray source optical system 50, which is provided with a plurality of stimulating ray sources for producing different laser beams 4, 4, . . . and selectively actuates one of the stimulating ray sources to produce the laser beam 4. The image read-out apparatus 100 still further comprises a photomultiplier 30 acting as photo detecting means for detecting the emitted light 25. The image read-out apparatus 100 also comprises optical means 60 for guiding the laser beam 4, which has been produced by the stimulating ray source optical system 50, toward the optical head 15 and guiding the emitted light 25 toward the photomultiplier 30.

The stimulating ray source optical system 50 comprises a first laser beam source 1 for producing a laser beam 4 having a wavelength of 640 nm. The stimulating ray source optical system 50 also comprises a second laser beam source 2 for producing a laser beam 4 having a wavelength of 532 nm. The stimulating ray source optical system 50 further comprises a third laser beam source 3 for producing a laser beam 4 having a wavelength of 473 nm. In this embodiment, the first laser beam source 1 is constituted of a semiconductor laser. Each of the second laser beam source 2 and the third laser beam source 3 is constituted of a semiconductor laser and a second harmonic generating device. The stimulating ray source optical system 50 still further comprises collimator lenses 5, 10, and 11 for collimating the laser beams 4, 4, 4, which have been produced respectively by the first laser beam source 1, the second laser beam source 2, and the third laser beam source 3. The stimulating ray source optical system 50 also comprises mirrors 6, 9, a first dichroic mirror 7, and a second dichroic mirror 8 for guiding each of the laser beams 4, 4, 4 toward the optical means 60.

The laser beam 4 having been produced by the first laser beam source 1 is collimated by the collimator lens 5, and the collimated laser beam 4 is reflected by the mirror 6. The first dichroic mirror 7 and the second dichroic mirror 8 are located in the optical path of the laser beam 4, which has been produced by the first laser beam source 1 and has then been reflected by the mirror 6. The first dichroic mirror 7 transmits only the laser beam 4 having a wavelength of 640 nm and reflects the light having a wavelength of 532 nm. The second dichroic mirror 8 transmits only the light having a wavelength of at least 532 nm and reflects the light having a wavelength of 473 nm. The laser beam 4, which has been produced by the first laser beam source 1 and has then been reflected by the mirror 6, passes through the first dichroic mirror 7 and the second dichroic mirror 8 and impinges upon the mirror 9.

The laser beam 4 having been produced by the second laser beam source 2 is collimated by the collimator lens 10, and the collimated laser beam 4 is reflected by the first dichroic mirror 7. The direction of the optical path of the laser beam 4 is thus changed by an angle of 90°. The laser beam 4 then passes through the second dichroic mirror 8 and impinges upon the mirror 9.

The laser beam 4 having been produced by the third laser beam source 3 is collimated by the collimator lens 11, and the collimated laser beam 4 is reflected by the second dichroic mirror 8. The direction of the optical path of the laser beam 4 is thus changed by an angle of 90°. The laser beam 4 then impinges upon the mirror 9.

The laser beam 4 impinging upon the mirror 9 is reflected by the mirror 9. The laser beam 4 then impinges upon a mirror 12 of the optical means 60, which will later be described in detail.

As illustrated in FIG. 2, the optical head 15 comprises a concave mirror 16 and an aspherical lens 17. The laser beam 4, which has traveled in parallel with the surface of the image carrier 22 and impinges upon the optical head 15, is reflected by the concave mirror 16 toward the image carrier 22. The laser beam 4, which has thus been reflected by the concave mirror 16, is converged by the a spherical lens 17 and onto the surface of the image carrier 22, which has been set on the glass base plate 21 of the stage 20. The light 25, which is emitted by the image carrier 22 when the image carrier 22 is exposed to the laser beam 4, is converged by the aspherical lens 17 and impinges upon the concave mirror 16. The emitted light 25 is then converged even further by the concave mirror 16 and is reflected by the concave mirror 16 so as to follow reversely the same optical path as the optical path of the laser beam 4. The emitted light 25 impinges as an approximately collimated beam upon a concave mirror 18 of the optical means 60 as will be described later.

The optical head 15 is located such that the beam waist of the laser beam 4 takes a position in the vicinity of the surface of the image carrier 22. A focal point F of the aspherical lens 17 is located a position on the side of the image carrier 22, which side is opposite to the optical head 15. In such cases, the light 25 emitted by the image carrier 22 cannot be collimated only with the refracting power of the aspherical lens 17 and therefore impinges in the divergent state upon the concave mirror 16. However, by the effect of the concave mirror 16, the emitted light 25 having passed through the aspherical lens 17 is converged even further by the concave mirror 16 and is reflected from the concave mirror 16 as an approximately collimated light beam. If the emitted light 25 is radiated out as a divergent light beam from the optical head 15, the problems will occur in that the amount of the emitted light 25 capable of being detected by the photomultiplier 30 via the optical means 60 becomes small, and therefore the read-out sensitivity becomes low. However, in cases where the optical head 15 comprising the concave mirror 16 and the aspherical lens 17 is employed as in this embodiment, the problems described above are capable of being eliminated.

The optical head 15 is capable of being moved in X and Y two-dimensional directions in FIG. 1 by a scanning mechanism, which will be described later. By the movement of the optical head 15 in the X and Y directions, the entire area of the image carrier 22 is capable of being scanned with the laser beam 4.

The optical means 60 comprises the mirror 12, a perforated mirror 14, and the concave mirror 18 for separating the laser beam 4 and the emitted light 25 from each other. The perforated mirror 14 is constituted of a concave mirror having a hole 13 at a center area. The optical means 60 also comprises a filter unit 28 for selectively transmitting the emitted light 25 toward the photomultiplier 30.

The laser beam 4, which has been reflected by the mirror 9 of the stimulating ray source optical system 50 and has impinged upon the mirror 12, is reflected by the mirror 12, passes through the hole 13 of the perforated mirror 14, and impinges upon the concave mirror 18. Also, the laser beam 4 impinging upon the concave mirror 18 is reflected by the concave mirror 18 and impinges upon the optical head 15.

Also, the emitted light 25, which has been emitted by the image carrier 22, has then been reflected by the concave mirror 16 of the optical head 15, and has thereafter impinged upon the concave mirror 18, is reflected by the concave mirror 18 and impinges upon the perforated mirror 14.

As illustrated in FIG. 3, the emitted light 25 impinging upon the perforated mirror 14 is reflected downwardly by the perforated mirror 14 and impinges upon the filter unit 28. The filter unit 28 filters out light having predetermined wavelengths. The emitted light 25 having passed through the filter unit 28 impinges upon the photomultiplier 30 and is photoelectrically detected by the photomultiplier 30.

As illustrated in FIG. 3, the filter unit 28 comprises four filter members 31a, 31b, 31c, and 31d. The filter unit 28 is capable of being moved by a motor (not shown) horizontally in FIG. 3.

The filter member 31a is utilized in cases where the image carrier 22 is a gel support or a transcription support. Specifically, the filter member 31a is utilized in cases where the fluoro chrome contained in the image carrier 22 is excited by the laser beam 4 having been produced by the first laser beam source 1, and the fluorescence, which is thus produced by the fluoro chrome as the emitted light 25, is detected. The filter member 31a is provided with a filter having the properties for filtering out light having a wavelength of 640 nm and transmitting only light having wavelengths longer than 640 nm.

The filter member 31b is utilized in cases where the image carrier 22 is the gel support or the transcription support. Specifically, the filter member 31b is utilized in cases where the fluoro chrome contained in the image carrier 22 is excitedly the laser beam 4 having been produced by the second laser beam source 2, and the fluorescence, which is thus produced by the fluoro chrome as the emitted light 25, is detected. The filter member 31b is provided with a filter having the properties for filtering out light having a wavelength of 532 nm and transmitting only light having wavelengths longer than 532 nm.

The filter member 31c is utilized in cases where the image carrier 22 is the gel support or the transcription support. Specifically, the filter member 31c is utilized in cases where the fluoro chrome contained in the image carrier 22 is excited by the laser beam 4 having been produced by the third laser beam source 3, and the fluorescence, which is thus produced by the fluoro chrome as the emitted light 25, is detected. The filter member 31c is provided with a filter having the properties for filtering out light having a wavelength of 473 nm and transmitting only light having wavelengths longer than 473 nm.

The filter member 31d is utilized in cases where the image carrier 22 is a stimulable phosphor sheet. Specifically, filter member 31d is utilized in cases where the stimulable phosphor contained in the stimulable phosphor sheet is stimulated by the laser beam 4 having been produced by the first laser beam source 1, and the light 25 emitted by the stimulable phosphor is detected. The filter member 31d is provided with a filter having the properties for filtering out light having a wavelength of 640 nm and transmitting only light having wavelengths falling within the wavelength range of the light 25 emitted by the stimulable phosphor.

The first laser beam source 1, the second laser beam source 2, or the third laser beam source 3 is selected in accordance with the kind of the image carrier 22 and the kind of the fluoro chrome. Also, the filter member 31a, 31b, 31c, or 31d corresponding to the selected laser beam source is selectively located in front of the photomultiplier 30. In this manner, the photomultiplier 30 is capable of photoelectrically detecting only the light which is to be detected.

The emitted light 25 is photoelectrically detected by the photomultiplier 30, and an analog image signal is thereby obtained. The analog image signal is fed into an analog-to-digital converter 33 and is converted into a digital image signal. The digital image signal is fed into an image signal processing unit 34.

Figure 4:
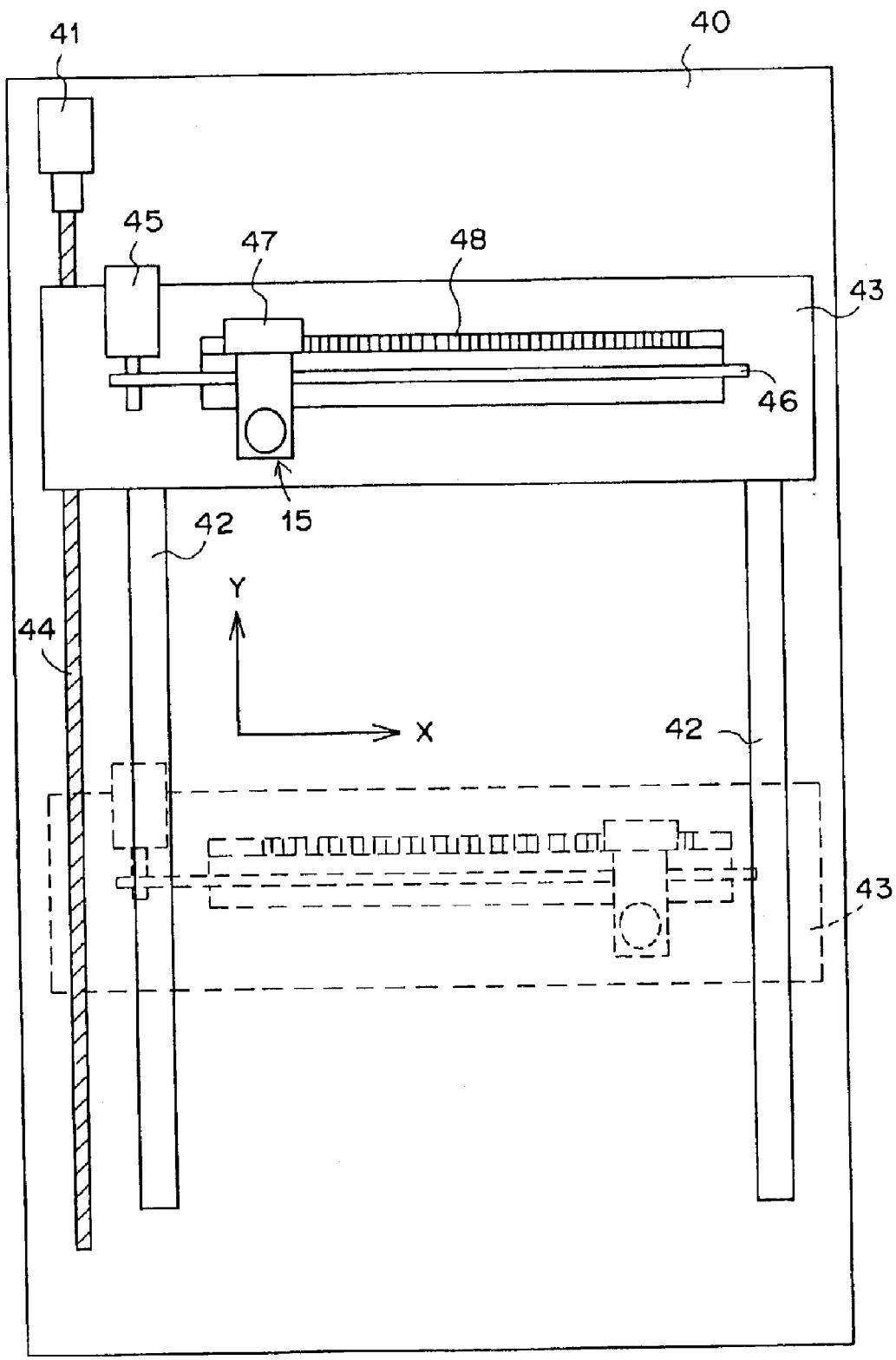
FIG. 4 is a schematic plan view showing a scanning mechanism for the optical head in the embodiment of FIG. 1.

FIG. 4 is a schematic plan view showing a scanning mechanism for the optical head 15. In FIG. 4, as an aid in facilitating the explanation, the optical system other than the optical head 15, the optical path of the laser beam 4, and the optical path of the emitted light 25 are not shown.

As illustrated in FIG. 4, the scanning mechanism for scanning the optical head 15 comprises a base 40. The scanning mechanism also comprises a sub-scanning pulse motor 41 and a pair of rails 42, 42, which are located on the base 40. The scanning mechanism further comprises an optical head support base 43, which is capable of moving on the rails 42, 42 and in the sub-scanning direction indicated by the arrow Y in FIG. 4.

The optical head support base 43 has a threaded hole (not shown). A threaded rod 44, which is rotated by the sub-scanning pulse motor 41, is engaged with the threaded hole of the optical head support base 43.

A main scanning pulse motor 45 is located on the movable optical head support base 43. The main scanning pulse motor 45 is capable of moving an endless belt 46. The optical head 15 is secured to the endless belt 46. When the endless belt 46 is moved by the main scanning pulse motor 45, the optical head 15 is moved by the endless belt 46 in the main scanning direction indicated by the arrow X in FIG. 4. The optical head 15 is provided with a linear encoder 47 for detecting the position of the optical head 15 with respect to the main scanning direction. Also, the optical head support base 43 is provided with slits 48, 48, . . . for the linear encoder 47.

The endless belt 46 is moved by the main scanning pulse motor 45 in the main scanning direction indicated by the arrow X. Also, the movable optical head support base 43 is moved by the sub-scanning pulse motor 41 in the sub-scanning direction indicated by the arrow Y. In this manner, the optical head 15 is moved in the main scanning direction indicated by the arrow X in FIG. 1 and FIG. 4 and in the sub-scanning direction indicated by the arrow Y in FIG. 1 and FIG. 4. As a result, the entire surface of the image carrier 22 is scanned with the laser beam 4.

This embodiment of the image read-out apparatus in accordance with the present invention is constituted such that the image read-out apparatus is capable of reading out an electrophoresis image of a denatured DNA having been labeled with the fluoro chrome, which image has been recorded on the gel support, the transcription support, or the like, and an autoradiography image concerning position information of the radioactive labeling substance, which image has been recorded on the stimulable phosphor layer of the stimulable phosphor sheet. The image carrier 22, from which the image is to be read out, may be the gel support or the transcription support. Alternatively, the image carrier 22, from which the image is to be read out, may be the stimulable phosphor sheet.

By way of example, the electrophoresis image of the denatured DNA having been labeled with the fluoro chrome is recorded on the transcription support in the manner described below.

Specifically, firstly, a plurality of DNA fragments containing DNA fragments of a target gene are subjected to separation and development with the electrophoresis on a gel support medium, and then converted into a single stranded DNA by denaturation with alkali treatment.

Thereafter, by the utilization of the known Southern blotting technique, the gel support medium and the transcription support are superposed one upon the other, and at least certain denatured DNA fragments among the aforesaid denatured DNA fragments are transcribed onto the transcription support. Also, the denatured DNA fragments having thus been transcribed are fixed on the transcription support with heat treatment and ultraviolet light irradiation.

Thereafter, the denatured DNA fragments, which have been fixed on the transcription support, and a probe having been prepared by labeling a DNA or an RNA, which is complementary to the DNA of the target gene, with the fluoro chrome, are subjected to hybridization with heat treatment. In this manner, renaturation of the duplex DNA or formation of a DNA-RNA hybrid is performed. By way of example, the probe is prepared by labeling the DNA or the RNA, which is complementary to the DNA of the target gene, with the fluoro chrome, such as Fluorescein (trade name), Rhodamine (trade name), or Cy5 (trade name). At this time, the denatured DNA fragments on the transcription support have been fixed, and therefore only the DNA fragments, which are complementary to the probe DNA or the probe RNA, undergo the hybridization with the probe and catch the probe labeled with the fluoro chrome. Thereafter, the probe having not formed the hybrid is washed off with an appropriate solution. On the transcription support, only the DNA fragments of the target gene form the hybrid with the fluoro chrome-labeled DNA or the fluoro chrome-labeled RNA and are thus imparted with the fluorescent label. In this manner, the electrophoresis image of the denatured DNA having been labeled with the fluoro chrome is recorded on the transcription support.

The position information of the radioactive labeling substance is recorded on the stimulable phosphor layer of the stimulable phosphor sheet in the manner described below. The term "position information" as used herein means at least one of various kinds of information principally containing the information representing the position of the radioactive labeling substance in the sample or the position of an aggregate of the radioactive labeling substance in the sample. For example, the term "position information" as used herein means one of various kinds of information, such as the information representing the position of the aggregate of the radioactive labeling substance in the sample, the information representing the shape of the aggregate of the radioactive labeling substance, the information representing the concentration of the radioactive labeling substance at its position, and the information representing the distribution of the radioactive labeling substance. Also, the term "position information" as used herein means an arbitrary combination of the various kinds of information described above.

By way of example, in cases where the Southern blot hybridization technique is utilized, the position information of the radioactive labeling substance in a gene is recorded on the stimulable phosphor layer of the stimulable phosphor sheet in the manner described below.

Specifically, firstly, a plurality of DNA fragments containing DNA fragments of a target gene are subjected to separation and development with the electrophoresis on a gel support medium, and then converted into a single stranded DNA by denaturation with alkali treatment.

Thereafter, by the utilization of the known Southern blotting technique, the gel support medium and the transcription support, which may be constituted of a nitrocellulose filter, or the like, are superposed one upon the other, and at least certain denatured DNA fragments among the aforesaid denatured DNA fragments are transcribed onto the transcription support. Also, the denatured DNA fragments having thus been transcribed are fixed on the transcription support with heat treatment and ultraviolet light irradiation.

Thereafter, the denatured DNA fragments, which have been fixed on the transcription support, and a probe having been prepared by, for example, labeling a DNA or an RNA, which is complementary to the DNA of the target gene, with the radio active labeling substance, are subjected to the hybridization with heat treatment. In this manner, renaturation of the duplex DNA or formation of a DNA-RNA hybrid is performed. At this time, the denatured DNA fragments on the transcription support have been fixed, and therefore only the DNA fragments, which are complementary to the probe DNA or the probe RNA, undergo the hybridization with the probe and catch the probe labeled with the radioactive labeling substance.

Thereafter, the probe having not formed the hybrid is washed off with an appropriate solution. On the transcription support, only the DNA fragments of the target gene form the hybrid with the DNA or the RNA having been labeled with the radioactive labeling substance and are thus imparted with the radioactive label. Thereafter, an exposure operation is performed by superposing the transcription support after being dried and the stimulable phosphor sheet one upon the other for a predetermined length of time. During the exposure operation, at least part of energy of the radiation, which is radiated out from the radioactive labeling substance located on the transcription support, is absorbed by the stimulable phosphor layer of the stimulable phosphor sheet. As a result, the position information of the radioactive labeling substance in the sample is stored as an image on the stimulable phosphor layer.

In cases where the laser beam 4 impinges upon the image carrier 22, which carries the image of the fluorescent substance on the gel support or the transcription support, the fluorescent substance is excited by the laser beam 4 to produce the fluorescence as the emitted light 25. Also, in cases where the laser beam 4 impinges upon the image carrier 22, which is constituted of the stimulable phosphor sheet carrying the radiation image stored thereon, the stimulable phosphor of the stimulable phosphor layer of the stimulable phosphor sheet is stimulated by the laser beam 4 to emit the light 25.

How an image read-out operation is performed by the aforesaid embodiment of the image read-out apparatus in accordance with the present invention will be described hereinbelow.

Firstly, how the autoradiography image concerning the position information of the radioactive labeling substance, which image has been recorded on the stimulable phosphor layer of the stimulable phosphor sheet, is read out from the stimulable phosphor sheet will be described hereinbelow.

The stimulable phosphor sheet acting as the image carrier 22 is placed on the glass plate 21 of the stage 20 of the image read-out apparatus. Thereafter, an instruction signal for the readout of the auto radiography image concerning the position information of the radioactive labeling substance, which image has been recorded on the stimulable phosphor layer of the stimulable phosphor sheet, is inputted by the operator from input means (not shown).

In accordance with the instruction signal, the filter unit motor is actuated in order to move the filter unit 28, such that the filter member 31*d* comprising the filter, which has the properties for filtering out light having a wavelength of 640 nm and transmitting only light having wavelengths falling within the wavelength range of the light 25 emitted by the stimulable phosphor, is located in the optical path of the emitted light 25.

Thereafter, the first laser beam source 1 is actuated to produce the laser beam 4 having a wavelength of 640 nm.

The laser beam 4 having been produced by the first laser beam source 1 is collimated by the collimator lens 5. The collimated laser beam 4 impinges upon the mirror 6 and is reflected by the mirror 6.

The laser beam 4 having been reflected by the mirror 6 passes through the first dichroic mirror 7 and the second dichroic mirror 8 and impinges upon the mirror 9.

The laser beam 4 impinging upon the mirror 9 is reflected by the mirror 9. The laser beam 4 then impinges upon the mirror 12 and is reflected by the mirror 12. The laser beam 4 having been reflected by the mirror 12 passes through the hole 13 of the perforated mirror 14 and impinges upon the concave mirror 18.

The laser beam 4 impinging upon the concave mirror 18 is reflected by the concave mirror 18, travels in parallel with the image carrier 22, and impinges upon the optical head 15.

The laser beam 4 impinging upon the optical head 15 is reflected by the concave mirror 16 toward the image carrier 22 and converged by the aspherical lens 17 onto the stimulable phosphor sheet, which is placed on the glass plate 21 of the stage 20.

As a result, the stimulable phosphor contained in the stimulable phosphor layer of the stimulable phosphor sheet is stimulated by the laser beam 4 to emit the light 25.

The light 25 emitted by the stimulable phosphor is converged by the aspherical lens 17 of the optical head 15. The emitted light 25 is converged even further by the concave mirror 16 and is reflected by the concave mirror 16 so as to follow reversely the same optical path as the optical path of the laser beam 4. The emitted light 25 thus impinges as the collimated beam upon the concave mirror 18.

The emitted light 25 impinging upon the concave mirror 18 is reflected by the concave mirror 18 and impinges upon the perforated mirror 14. The emitted light 25 impinging upon the perforated mirror 14 is reflected by the perforated mirror 14 and impinges upon the filter member 31*d* of the filter unit 28.

The filter member 31*d* comprises the filter, which has the properties for filtering out light having a wavelength of 640 nm and transmitting only light having wavelengths falling within the wavelength range of the light 25 emitted by the stimulable phosphor. Therefore, the light having a wavelength of 640 nm and acting as the stimulating rays is filtered out, and only the light having wavelengths falling within the wavelength range of the light 25 emitted by the stimulable phosphor passes through the filter of the filter member 31*d* and is photoelectrically detected by the photomultiplier 30.

As described above, the optical head 15 is moved by the main scanning pulse motor 45, which is located on the movable optical head support base 43. Specifically, the optical head 15 is moved on the optical head support base 43 in the main scanning direction indicated by the arrow X and in the sub-scanning direction indicated by the arrow Y. As a result, the entire surface of the stimulable phosphor sheet is scanned with the laser beam 4. The light 25 thus emitted by the stimulable phosphor contained in the stimulable phosphor layer of the stimulable phosphor sheet is photoelectrically detected by the photomultiplier 30. In this manner, the autoradiography image concerning the position information of the radioactive labeling substance, which image has been recorded on the stimulable phosphor layer of the stimulable phosphor sheet, is capable of being read out, and an analog image signal representing the autoradiography image is capable of being formed.

The analog image signal obtained from the photomultiplier 30 is converted by the analog-to-digital converter 33 into the digital image signal. The digital image signal is fed into the image signal processing unit 34.

How the fluorescence image, which has been recorded on the transcription support or the gel support, is readout from the transcription support or the gel support will be described hereinbelow.

The transcription support or the gel support acting as the image carrier 22 is placed on the glass plate 21 of the stage 20 of the image read-out apparatus. Thereafter, an instruction signal for specifying the kind of the fluorescent labeling substance, with which the sample has been labeled, and instructing the readout of the fluorescence image carried on the transcription support or the gel support is inputted by the operator from the input means (not shown). In accordance with the inputted instruction signal, the laser beam source and the filter member to be used are determined.

For example, in cases where the sample has been labeled with Rhodamine (trade name), which is capable of being excited most efficiently by the laser beam having a wavelength of 532 nm, the second laser beam source 2 and the filter member 31*b* are selected.

The filter unit motor is actuated in order to move the filter unit 28, such that the filter member 31*b* comprising the filter, which has the properties for filtering out light having a wavelength of 532 nm and transmitting only light having wavelengths longer than 532 nm, is located in the optical path of the fluorescence, which is produced as the emitted light 25.

Thereafter, the second laser beam source 2 is actuated to produce the laser beam 4 having a wavelength of 532 nm.

The laser beam 4 having been produced by the second laser beam source 2 is collimated by the collimator lens 10. The collimated laser beam 4 impinges upon the first dichroic mirror 7 and is reflected by the first dichroic mirror 7.

The laser beam 4 having been reflected by the first dichroic mirror 7 passes through the second dichroic mirror 8 and impinges upon the mirror 9.

The laser beam 4 impinging upon the mirror 9 is reflected by the mirror 9. The laser beam 4 then impinges upon the mirror 12 and is reflected by the mirror 12. The laser beam 4 having been reflected by the mirror 12 passes through the hole 13 of the perforated mirror 14 and impinges upon the concave mirror 18.

The laser beam 4 impinging upon the concave mirror 18 is reflected by the concave mirror 18, travels in parallel with the image carrier 22, and impinges upon the optical head 15.

The laser beam 4 impinging upon the optical head 15 is reflected by the concave mirror 16 toward the image carrier 22 and converged by the aspherical lens 17 onto the transcription support or the gel support, which is placed on the glass plate 21 of the stage 20.

As a result, Rhodamine, which acts as the fluorescent substance and is contained in the transcription support or the gel support, is excited by the laser beam 4 to produce the fluorescence 25.

The fluorescence 25 having been produced by Rhodamine is converged by the aspherical lens 17 of the optical head 15. The fluorescence 25 is converged even further by the concave mirror 16 and is reflected by the concave mirror 16 so as to follow reversely the same optical path as the optical path of the laser beam 4. The fluorescence 25 thus impinges as the collimated beam upon the concave mirror 18.

The fluorescence 25 impinging upon the concave mirror 18 is reflected by the concave mirror 18 and impinges upon the perforated mirror 14. The fluorescence 25 impinging upon the perforated mirror 14 is reflected by the perforated mirror 14 and impinges upon the filter member 31b of the filter unit 28.

The filter member 31b comprises the filter, which has the properties for filtering out light having a wavelength of 532 nm and transmitting only light having wavelengths longer than 532 nm. Therefore, the light having a wavelength of 532 nm and acting as the stimulating rays is filtered out, and only the light having wavelengths falling within the wavelength range of the fluorescence 25 produced by Rhodamine passes through the filter of the filter member 31b and is photoelectrically detected by the photomultiplier 30.

As described above, the optical head 15 is moved by the main scanning pulse motor 45, which is located on the movable optical head support base 43. Specifically, the optical head 15 is moved on the optical head support base 43 in the main scanning direction indicated by the arrow X and in the sub-scanning direction indicated by the arrow Y. As a result, the entire surface of the transcription support or the gel support is scanned with the laser beam 4. The fluorescence 25 thus produced by Rhodamine, which is contained in the transcription support or the gel support and with which the sample has been labeled, is photoelectrically detected by the photomultiplier 30. In this manner, the fluorescence image of Rhodamine acting as the fluorescent substance, which image has been recorded on the transcription support or the gel support, is capable of being read out, and an analog image signal representing the fluorescence image is capable of being formed.

The analog image signal obtained from the photomultiplier 30 is converted by the analog-to-digital converter 33 into the digital image signal. The digital image signal is fed into the image signal processing unit 34.

The image read-out apparatus in accordance with the present invention is not limited to the embodiment described above and may be embodied in various other ways.

For example, in the embodiment described above, the transcription support or the gel support, on which the electrophoresis image of the gene has been recorded with the fluorescence image detecting system utilizing the Southern blot hybridization technique, and the stimulable phosphor sheet, on which the radiation image has been recorded with the autoradiography image detecting system, are employed as the image carriers. Also, the electrophoresis image and the radiation image are read out photoelectrically. However, the image read-out apparatus in accordance with the present invention is not limited to the cases where the electrophoresis image and the radiation image are read out. For example, the image read-out apparatus in accordance with the present invention is also applicable to the readout of a different kind of an image of a fluorescent substance, which has been recorded on the transcription support or the gel support with the fluorescence image detecting system, and an image of a fluorescent substance for use in separation and identification of proteins or evaluation of molecular weights and characteristics of proteins. Further, the image read-out apparatus in accordance with the present invention is applicable to the readout of a different kind of an autoradiography image having been recorded on the stimulable phosphor layer of the stimulable phosphor sheet, such as an autoradiography image having been formed with thin-layer chromatography (TLC) for proteins and having been recorded on the stimulable phosphor layer of the stimulable phosphor sheet, an autoradiography image having been recorded on the stimulable phosphor layer of the stimulable phosphor sheet with polyacrylamide gel electrophoresis for performing separation and identification of proteins or evaluation of molecular weights and characteristics of proteins, or an autoradiography image having been recorded on the stimulable phosphor layer of the stimulable phosphor sheet for use in research of, for example, pathways and conditions of metabolism, absorption, and excretion of an administered substance in an experimental mouse. Furthermore, the image read-out apparatus in accordance with the present invention is applicable to the readout of an electron beam transmission image or an electron beam diffraction image of a metal sample or a nonmetal sample, which image has been formed with an electron microscope and recorded on the stimulable phosphor layer of the stimulable phosphor sheet. Also, the image read-out apparatus in accordance with the present invention is applicable to the readout of an electron microscope image of an organism tissue. Further, the image read-out apparatus in accordance with the present invention is applicable to the readout of a radiation diffraction image of a metal sample or a nonmetal sample, which image has been recorded on the stimulable phosphor layer of the stimulable phosphor sheet. Furthermore, the image read-out apparatus in accordance with the present invention is applicable to the readout of a chemiluminescence image having been recorded on the stimulable phosphor layer of the stimulable phosphor sheet.

Also, the embodiment described above is provided with the first laser beam source 1, the second laser beam source 2, and the third laser beam source 3. However, the image read-out apparatus in accordance with the present invention need not necessarily be provided with the three laser beam sources. Specifically, it is sufficient for the image read-out apparatus in accordance with the present invention to be constituted such that the image read-out apparatus is capable of reading both the fluorescence image, which is carried on the transcription support or the gel support, and the image having been recorded on the stimulable phosphor layer of the stimulable phosphor sheet, such as the autoradiography image concerning the position information of the radioactive labeling substance, which image has been recorded on the stimulable phosphor layer of the stimulable phosphor sheet, the electron beam transmission image or the electron beam diffraction image of a metal sample or a nonmetal sample, which image has been recorded on the stimulable phosphor layer of the stimulable phosphor sheet, the electron microscope image of an organism tissue, the radiation diffraction image of a metal sample or a nonmetal sample, which image has been recorded on the stimulable phosphor layer of the stimulable phosphor sheet, or the chemiluminescence image having been recorded on the stimulable phosphor layer of the stimulable phosphor sheet. For example, in the image read-out apparatus in accordance with the present invention, the second laser beam source 2 may be omitted. Specifically, the image read-out apparatus in accordance with the present invention may be provided with only the first laser beam source 1, such that the image read-out apparatus is capable of reading a fluorescence image, which has been formed by labeling the sample with, for example, Cy-5 capable of being excited efficiently by the laser beam 4 having a wavelength of 640 nm, and the image having been recorded on the stimulable phosphor layer of the stimulable phosphor sheet, such as the autoradiography image concerning the position information of the radioactive labeling substance, the electron microscope image, the radiation diffraction image, or the chemiluminescence image, which image has been recorded on the stimulable phosphor layer of the stimulable phosphor sheet.

Further, in the embodiment described above, the photomultiplier 30 is utilized as the photodetector in order to perform the photoelectric detection of the light 25 emitted by the image carrier 22 or the fluorescence 25 produced by the image carrier 22. However, the photodetector utilized in the image read-out apparatus in accordance with the present invention is not limited to the photomultiplier 30 and may be selected from various other photodetectors capable of photoelectrically detecting the emitted light 25 or the fluorescence 25. For example, the photodetector may be a photodiode image sensor or a CCD image sensor.

Furthermore, the embodiment described above is provided with the scanning mechanism for moving the optical head 15 in two-dimensional directions. Alternatively, the optical head 15 maybe kept stationary, and the image read-out apparatus may be provided with a scanning mechanism for moving the stage 20 in two-dimensional directions.

What is claimed is:

1. An image read-out method, comprising the steps of:
   i) supporting an image carrier, which carries an image thereon, on a stage,
   ii) producing a stimulating ray beam by at least one stimulating ray source,
   iii) irradiating the stimulating ray beam, which has been produced by the stimulating ray source, onto the image carrier, which has been supported on the stage, by use of an optical head, the stimulating ray beam causing the image carrier to emit light carrying information of the image carried on the image carrier,
   iv) collecting the light, which is emitted by the image carrier, and guiding the light toward photo detecting means, the light collection and the light guiding being performed by the optical head,
   v) photoelectrically detecting the light, which is emitted by the image carrier, with the photo detecting means, and
   vi) moving at least either one of the optical head and the stage with respect to the other and in two-dimensional directions along a plane parallel with the other,
   wherein the optical head comprises:
   a) a concave mirror for reflecting the stimulating ray beam, which has been produced by the stimulating ray source and travels in parallel with the stage, toward the image carrier, and
   b) a lens for converging the stimulating ray beam, which has been reflected from the concave mirror, and causing the converged stimulating ray beam to impinge upon the image carrier, and
   the lens and the concave mirror of the optical head guide the light, which is emitted by the image carrier, toward the photo detecting means.

2. A method as defined in claim 1 wherein the image carrier is a support, on which an image of a fluorescent substance formed with a fluorescence image detecting system is carried.

3. A method as defined in claim 1 wherein the image carrier is a stimulable phosphor sheet, on which an autoradiography image is carried.

4. A method as defined in claim 1 wherein the image carrier is a stimulable phosphor sheet, on which an electron microscope image is carried.

5. A method as defined in claim 1 wherein the image carrier is a stimulable phosphor sheet, on which a radiation diffraction image is carried.

6. A method as defined in claim 1 wherein the image carrier is a stimulable phosphor sheet, on which a chemiluminescence image is carried.

7. A method as defined in claim 1, wherein a focal point of the lens is located on a side of the image carrier opposite from the optical head.

8. An image read-out apparatus, comprising:
   i) at least one stimulating ray source for producing a stimulating ray beam,
   ii) a stage for supporting an image carrier, which carries an image thereon,
   iii) photo detecting means for photoelectrically detecting light, which is emitted by the image carrier, and
   iv) an optical head for:
   irradiating the stimulating ray beam, which has been produced by the stimulating ray source, onto the image carrier, which has been supported on the stage, the stimulating ray beam causing the image carrier to emit light carrying information of the image carried on the image carrier, and
   collecting the light, which is emitted by the image carrier, and guiding the light toward the photo detecting means, and
   v) means for moving at least either one of the optical head and the stage with respect to the other and in two-dimensional directions along a plane parallel with the other,
   wherein the optical head comprises:
   a) a concave mirror for reflecting the stimulating ray beam, which has been produced by the stimulating ray source and travels in parallel with the stage, toward the image carrier, and
   b) a lens for converging the stimulating ray beam, which has been reflected from the concave mirror, and causing the converged stimulating ray beam to impinge upon the image carrier, and
   the lens and the concave mirror of the optical head guide the light, which is emitted by the image carrier, toward the photo detecting means.

9. An apparatus as defined in claim 8 wherein the image carrier is a support, on which an image of a fluorescent substance formed with a fluorescence image detecting system is carried.

10. An apparatus as defined in claim 8 wherein the image carrier is a stimulable phosphor sheet, on which an autoradiography image is carried.

11. An apparatus as defined in claim 8 wherein the image carrier is a stimulable phosphor sheet, on which an electron microscope image is carried.

12. An apparatus as defined in claim 8 wherein the image carrier is a stimulable phosphor sheet, on which a radiation diffraction image is carried.

13. An apparatus as defined in claim 8 wherein the image carrier is a stimulable phosphor sheet, on which a chemiluminescence image is carried.

14. An apparatus as defined in claim 8, further comprising an optical encoder which detects a position of the optical head in a main scanning direction.

15. An apparatus as defined in claim 8, wherein the lens comprises an aspherical lens.

* * * * *